United States Patent [19]
Hotta et al.

[11] Patent Number: 5,894,353
[45] Date of Patent: Apr. 13, 1999

[54] OPTICAL MEASURING METHOD, OPTICAL MEASURING APPARATUS AND IMAGE FORMING APPARATUS

[75] Inventors: Hiroyuki Hotta; Seigo Makida; Yoshihiko Sakai; Hisao Ito, all of Ashigarakami-gun, Japan

[73] Assignee: Fuji Xerox Co., Ltd., Tokyo, Japan

[21] Appl. No.: 08/982,799

[22] Filed: Oct. 14, 1997

[30] Foreign Application Priority Data

Oct. 18, 1996 [JP] Japan .................................. 8-297218
Jul. 24, 1997 [JP] Japan .................................. 9-198373

[51] Int. Cl.$^6$ .................................................. G01N 21/47
[52] U.S. Cl. .................................... 356/446; 356/429
[58] Field of Search ................................ 356/446, 429

[56] References Cited

U.S. PATENT DOCUMENTS

| | | |
|---|---|---|
| 4,715,718 | 12/1987 | Evans . |
| 4,756,619 | 7/1988 | Gerlinger et al. ............... 356/446 |
| 4,919,535 | 4/1990 | Hohberg et al. ............... 356/446 |
| 5,030,841 | 7/1991 | Wampfler ........................ 356/429 |

FOREIGN PATENT DOCUMENTS

| | | |
|---|---|---|
| 209 860 | 1/1987 | European Pat. Off. . |
| 234 579 | 9/1987 | European Pat. Off. . |
| 284 090 | 9/1988 | European Pat. Off. . |
| 299 314 | 1/1989 | European Pat. Off. . |
| 406 968 | 1/1991 | European Pat. Off. . |
| 3413838 | 10/1984 | Germany ........................ 356/446 |
| A-63-16247 | 1/1963 | Japan . |

OTHER PUBLICATIONS

"Apparatus And Method For Film Thickness And Optical Constant Determination," *Ibm Technical Disclosure Bulletin*, vol. 31, No. 8 Jan. 1989, pp. 363–368.

Primary Examiner—Richard A. Rosenberger
Attorney, Agent, or Firm—Oliff & Berridge, PLC

[57] ABSTRACT

A specific reflection area 42 on a paper surface 37a is irradiated with light from a light source 41 via nor not via a lens 43. A photoelectric conversion element 44 is placed on a focal surface in the rearward of the lens 43 and out of the light reflected (including scattering light and diffusion light) from the reflection area 42 on the paper surface 37a, only the whole light reflected within a predetermined angular range is received by the photoelectric conversion element 44 via the lens 43. The density of the image formed on the paper surface 37a is measured from the light reception output. When the paper surface 37a is irradiated with light from the light source 41 via the lens 43, the light source 41 is placed backward from the focal surface 43b in the rearward of the lens 43.

25 Claims, 13 Drawing Sheets

OPTICAL MEASURING METHOD, OPTICAL MEASURING APPARATUS AND IMAGE FORMING APPARATUS

BACKGROUND OF THE INVENTION

1. Field of the Invention

The present invention relates to an optical measuring method and an optical measuring apparatus for making possible the precise measurement of the quality of printed images that are output in an image forming apparatus (image output apparatus) such a color printer. The present invention also relates to an image forming apparatus which has a built-in optical measuring apparatus and is capable of image quality control by feeding back the measured results.

2. Description of the Related Art

With the progress of network technology centering on computers, network printers, for example, printers as image forming apparatus connected to networks have come into wide use rapidly. As the outputting of color images becomes popular, color printers are being increasingly developed now and so is a demand for improvement in the stabilization and uniformization of color image quality among a plurality of color printers.

In order to deal with such a demand, there arises the necessity of measuring the image quality of images that have been output, particularly color difference in the case of color images, and feeding back the measured results to each process step of forming images. Importance has specifically been attached to technology of using printers having built-in measuring apparatus so as to monitor the quality of output images on-line and to feed back the measured results. Consequently, a growing demand is for precision, low-cost, though small-sized, measuring apparatus to be developed as those fit for use in printers.

As far as a image quality monitor is concerned, a measuring apparatus called an X-rite capable of precise image measurement is now in wide use as what is used to make measurement off-line in such a state that an image forming medium such as paper is fixed.

However, unlike the aforementioned X-rite, no on-line precision color measuring apparatus has been put to practical use yet. This is due to the fact that precise measurement is impossible as it has posed a serious problem that in the case of on-line color measurement, the paper surface of paper as an image forming medium to be examined or an object of measurement is caused to undergo vertically fluctuating movement, that is, fluctuating movement in a direction perpendicular to the direction in which the paper is moved forward by a conveyer system.

When an optical system comprising a light source, a lens and a light reception element (photoelectric conversion element) in combination is used as used in the aforementioned X-rite to examine the paper surface making vertically fluctuating movement, for example, when the paper surface makes a vertically fluctuating movement of about 1 mm, the quantity of light received by the light reception element fluctuates because of reflection and scattering on the paper surface. Therefore, the output of the light reception element varies by about 15% and causes a great error to the output of the light reception element, thus rendering infeasible precise color measurement.

There has also been proposed a measuring apparatus for measuring colors on-line by correcting the vertically fluctuating movement of the paper surface like that. This apparatus is, as shown in FIG. 20, constituted of a characteristic measuring unit 1, a distance measuring unit 2 and a distance correction calculating unit 3.

The characteristic measuring unit 1 employs a color measuring sensor in order to measure the colors of a color image formed on paper 4 when the paper 4 as an object of measurement is conveyed in a direction of an arrow and supplies the measured color output to the distance correction calculating unit 3.

The distance measuring unit 2 is provided backward from the characteristic measuring unit 1 in the direction in which the paper 4 is conveyed and employs a distance detection sensor in order to measure the vertically fluctuating movement of the paper 4 at that position. Then the distance measuring unit 2 supplies the output of the measured vertically fluctuating movement to the distance correction calculating unit 3. The distance D between the characteristic measuring unit 1 and the distance measuring unit 2 is 70 mm, for example.

The distance correction calculating unit 3 corrects the measured color output from the characteristic measuring unit 1 using the output of the measured vertically fluctuating movement of the paper 4 from the distance measuring unit 2 and eliminates the influence of the vertically fluctuating movement of the paper 4. Further, the distance correction calculating unit 3 outputs the corrected measured color output as the measured result.

On the other hand, Japanese Patent Laid-Open No. 16247/1988 discloses a diffusion reflectance measuring apparatus which is said to be substantially free from the influence of the distance between the measuring apparatus and a sample (object of measurement) as long as the measured results are within a predetermined range. This apparatus is designed to accomplish the object by uniformizing the intensity of illuminating light on a surface to be examined. FIG. 21 shows a schematic construction of this measuring apparatus.

As shown in FIG. 21, the measuring apparatus above employs a point source 11 as a light source, which is placed at the focal position of a condenser lens 12, whereby rays of light emitted from the point source 11 become parallel rays of light by means of the condenser lens 12 and are incident on the paper surface 10b of paper conveyed in the direction of an arrow 10a. At this time, a range W of light illumination on the paper surface 10b is set greater than a measuring range m. Then the light reflected from the measuring range m on the paper surface 10b is received by the edge face 14a of an optical fiber 14.

The method described in the above publication is intended to maintain the illumination intensity substantially constantly in the measuring range m smaller than the range W of light illumination by making the parallel rays of light incident with respect to the paper surface 10b, irrespective of the distance between the point source 11 and the edge face 14a of the optical fiber. By maintaining the illumination intensity constantly, the measured result is set substantially free from the influence of the distance between the paper surface 10b and the edge face 14a of the optical fiber even the movement of the paper surface 10b vertically fluctuates within a predetermined range ≈d.

In the case of such a measuring apparatus of FIG. 20, color and distance measurement at each place intended for measurement cannot be made simultaneously because the characteristic measuring unit 1 and the distance measuring unit 2 have to be separated by the distance D from each other in the direction in which the paper is conveyed. Consequently, precise correction is hardly made and this results in greatly restricting the possibility of increasing the precision of the measured color output.

3

In view of the construction of the apparatus, since the characteristic measuring unit 1 and the distance measuring unit 2 together with the correcting calculation are essential, the shortcoming is that the apparatus tends to become large-scale and costly.

The method as disclosed in Japanese Patent Laid-Open No. 16247/1988 and shown in FIG. 21 uses the point source 11 as a light source and the condenser lens 12 for forming parallel rays of light so as to maintain the illumination intensity substantially constantly on the measuring paper surface 10b, whereby to obtain the measured result unaffected by the vertically fluctuating movement of the paper surface 10b. However, the originally nonexistent of a perfect point source results in making unavailable not only the uniform quantity of light but also parallel rays of light even though the point source 11 is placed at the focal position of the condenser lens 12. For this reason, the illumination intensity on the paper surface 10b is caused to vary by the vertically fluctuating movement of the paper surface 10b.

Since it has also been arranged that the rays of light reflected from the paper surface 10b are focussed into an image on the edge face 14a of the optical fiber via the lens 13, the image forming point deviates from the edge face 14a of the optical fiber likewise when the position of the reflection point as the movement of the paper surface 10b vertically fluctuates. After all, this method described in the above publication renders hardly obtainable the measured result unaffected by the vertically fluctuating movement of the paper surface 10b.

In addition to the aforementioned method, it is also considered feasible as one of the general measures taken to suppress the vertically fluctuating movement of a paper surface to press down paper by means of rollers. However, there are physical limitations to pressing down the paper strongly because the toner image formed on the paper surface has to be prevented from being peeled off or deviated. Even if the paper is allowed to be pressed down strongly, the vertically fluctuating movement of the paper would be impossible to decrease to zero; in other words, at least about several 100 μm still remain and consequently the output of the light reception element varies, thus making a precise measured output unobtainable.

SUMMARY OF THE INVENTION

In view of the foregoing problems, an object of the present invention is to make not only possible precise measurement which is unaffected by the fluctuating movement, if any, of a paper surface, for example, as an object of measurement but also producible a small-sized, less costly measuring apparatus.

An optical measuring method according to the present invention using a light source, a lens and an photoelectric conversion element which are disposed in such a manner that their relative positions are made mutually constant, comprises the steps of irradiating an object of measurement with light from the light source, causing the photoelectric conversion element to receive the light reflected from the object of measurement via the lens, and measuring the characteristics concerning the object of measurement from the light reception output of the photoelectric conversion element, wherein a specific area as an optional part of the area for the light passed through the lens and reflected from the object of measurement is set; and only the whole light reflected from the object of measurement within an angular range corresponding to the specific area is received by the photoelectric conversion element via the lens so as to make the total quantity of light received by the photoelectric conversion element an output of the photoelectric conversion element.

In this case, the object of measurement may be irradiated with light from the light source not via the lens or otherwise the object of measurement may be irradiated with light from the light source via the lens. In the latter case, the light source is preferably placed farther from the lens than the photoelectric-conversion-element-side focal surface of the lens.

In any one of the cases above, the photoelectric conversion element which makes the area of the specific area a light reception area may be installed on the photoelectric-conversion-element-side focal surface of the lens. The specific area is an opening and only light reflected from the object of measurement and passed through the opening may be received by the photoelectric conversion element. A condenser lens for making only light passed through the specific area incident on the photoelectric conversion element may otherwise be installed in the position of the specific area.

"Reflection" in the present invention not only means regular reflection but also includes scattering and diffusion.

With the arrangement above, out of the light reflected from the object of measurement (including the scattered light and diffusion light as described above), only light entering the specific angular range determined by a specific area with respect to the direction of optical axis of the lens is gathered in the specific area set on the photoelectric-conversion-element-side focal surface (hereinafter a rear-side focal surface) of the lens and only that light is received by the photoelectric conversion element.

In other words, out of the light reflected from the object of measurement, only light entering the specific angular range with respect to the direction of optical axis of the lens is incident on the photoelectric conversion element and the quantity of light received by the photoelectric conversion element is not affected by the fluctuating movement, if any, of the object of measurement, for example, paper surface.

The above and other objects and features of the present invention will be more apparent from the following description taken in conjunction with the accompanying drawings.

DETAILED DESCRIPTION OF THE PREFERRED EMBODIMENTS

Figure 3:
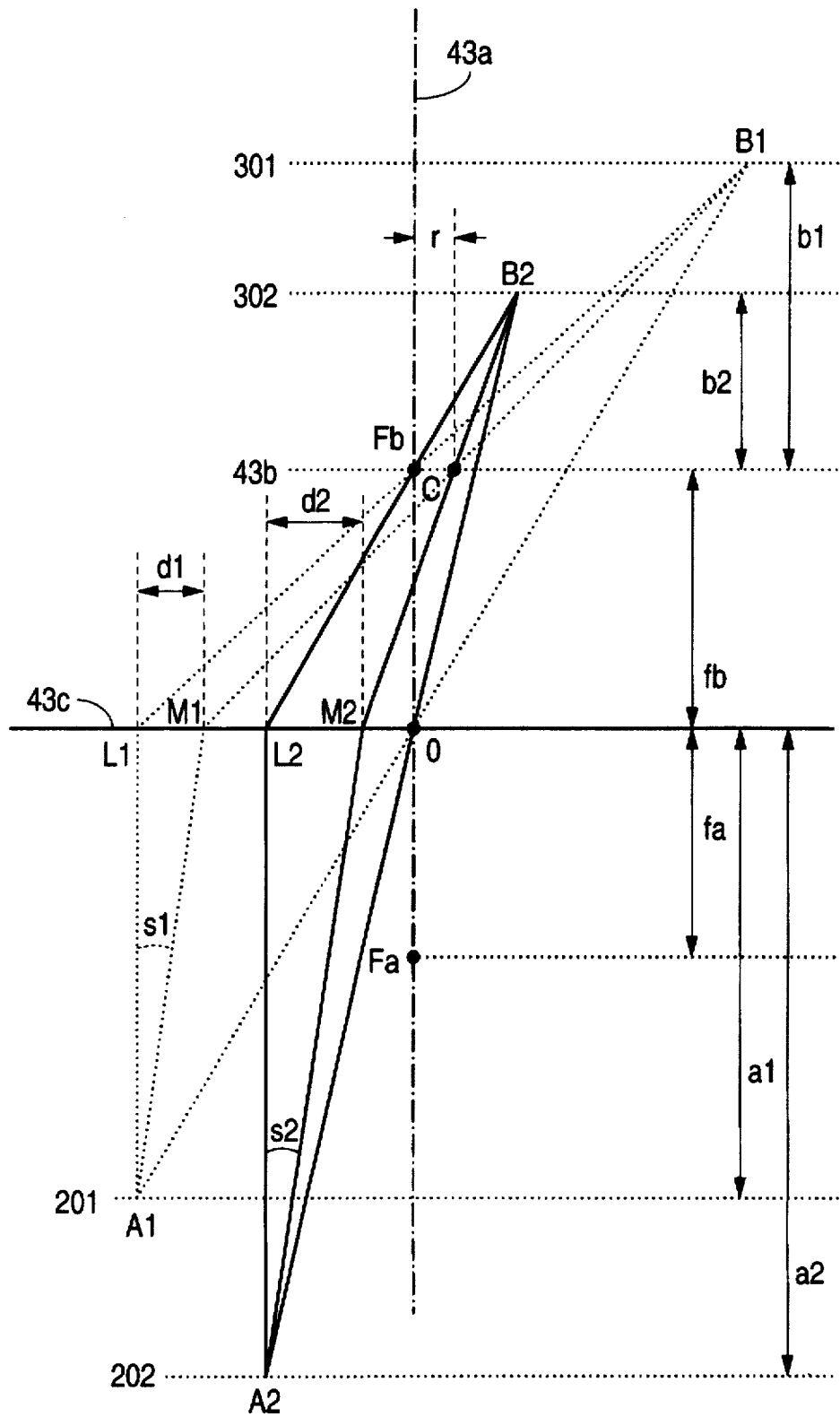
FIG. 3 is a diagram illustrating the principle of an optical measuring method according to the present invention.

First, referring to FIG. 3, there will be given a description of the theory of the present invention. FIG. 3 shows such a state that the light reflected from a paper surface as an example of an object of measurement is passed through a lens before being incident on a photoelectric conversion element installed on a focal surface in the rearward of the lens. As shown in FIG. 3, light incident on the photoelectric conversion element remains undependent on the vertically fluctuating movement of the paper surface. For convenience of explanation, however, the lens is assumed to be free from aberration, and the thickness and width of the lens are considered to be zero and infinite in FIG. 3.

In FIG. 3, a point 0 designates the center of the lens; an axis 43a, the optical axis of the lens; and a plane 43c, the position of the lens. Paper surfaces 201, 202 indicate the positions of the fluctuating movement of the paper surface, and image forming surfaces 301, 302 indicate image-forming surface positions corresponding to the fluctuating paper surface positions 201, 202. Further, a point Fa designates the paper-surface-side focus of the lens; a point Fb, the photoelectric-conversion-element-side focus of the lens (rear-side focus); a distance fa, the focal length of the lens as viewed on the paper surface side; a distance fb, the focal length of the lens as viewed on the photoelectric conversion element side; a point C, the end of the light reception area of the photoelectric conversion element; and a distance r, the distance between the end C of the light reception area and the rear side focus Fb of the lens.

In consideration of the light reflected from reflection points A1, A2 on the different paper surface positions 201, 202 in the direction of the optical axis 43a of the lens, passed through the lens and formed into images at image forming points B1, B2 on the image-forming surface positions 301, 302, reflection angles (angles with respect to the direction of the optical axis 43a) at the reflection points A1, A2 are defined as s1, s2 when the light is passed the end C of the light reception area of the photoelectric conversion element, respectively.

Further, the distance between the paper surface positions 201, 202 and the lens is represented by a1, a2; the distance between the rear-side focal surface 43b and the image-forming surface positions 301, 302 is represented by b1, b2; and points at which rays of light parallel to the optical axis 43a out of the light reflected from the reflection points A1, A2 pass through the lens surface are represented by L1, L2. Further, points at which the light reflected from the reflection points A1, A2, passed the end C of the light reception area of the photoelectric conversion element and formed into images at the image forming points B1, B2 pass through the lens surface are represented by M1, M2. Further, the distance between the points L1, M1 is represented by d1; and the distance between the points L2, M2 by d2.

From the Newton's formula in this image forming system, the following is established:

$$(a1-fa)(fa)=fb\cdot b1 \qquad (1)$$

$$(a2-fa)(fa)=fb\cdot b2 \qquad (2)$$

From the similarity between triangles B1L1M1 and B1FbC, and the similarity between triangles B2L2M2, B2FbC, the following is established:

$$r/b1=d1/(b1+fb) \qquad (3)$$

$$r/b2=d2/(b2+fb) \qquad (4)$$

In triangles A1L1M1 and A2L2M2, further, the following is established by the use of angles s1, s2:

$$d1=a1\cdot\tan(s1) \qquad (5)$$

$$d2=a2\cdot\tan(s2) \qquad (6)$$

When the equations (5), (6) are substituted for (3), (4), respectively, the following is obtainable:

$$a1=(b1+fb)r/(b1\cdot\tan(s1)) \qquad (7)$$

$$a2=(b2+fb)r/(b2\cdot\tan(s2)) \qquad (8)$$

When the equations (7), (8) are substituted for (1), (2), respectively, the following is obtainable:

$$r/\tan(s1)=fa \qquad (9)$$

$$r/\tan(s2)=fa \qquad (10)$$

From the equations (9), (10), the following is led:

$$s1=s2 \qquad (11)$$

When the above process is generalized by taking into consideration the light reflected from reflection points Ai such as the reflection points A1, A2 on the respective paper surface positions 20i (i=1, 2, 3 . . . ) of the paper surface whose movement fluctuates in the direction of the optical axis 43a such as the paper surface positions 201, 202, passed through the lens and formed into images at the respective image forming points Bi such as the image forming points B1, B2 on the respective image-forming surface positions 30i such as the image-forming surface positions 301, 302, a reflection angle si is kept constant at all times regardless of other parameters, given the reflection angle si at the reflection point Ai at the time the light passes the end C of the light reception area of the photoelectric conversion element.

In other words, as the movement of the paper surface fluctuates, a reflection area on the paper surface moves and even when the reflection point Ai is moved, the reflection angle si is kept constant at all times. On condition that reflection (including scattering and diffusion) occurs ideally, the number of rays of light contained in the reflection angle si is considered constant when a state at the reflection point Ai is similar, so that the quantity of light incident between Fb–C in the light reception area of the photoelectric conversion element becomes accurate in accordance with the state at each reflection point Ai without depending on the distance a between the paper surface and the lens and the distance between the paper surface and the photoelectric conversion element.

Therefore, the light reflected from the specific area of the paper surface and incident on the photoelectric conversion element corresponds to the state of that area without depending on the distance between the paper surface and the photoelectric conversion element.

Although each line segment is expressed on the plane in FIG. 3, an actual optical system is considered to be a rotary body centering on the optical axis 43a of the lens. In other words, the Fb–C length r of the light reception area of the photoelectric conversion element need not necessarily be constant like the radius of a circle centering on the optical axis 43a of the lens, and the light reception area of the photoelectric conversion element may be in any desired shape, circular or square, for example.

Moreover, the center position of the photoelectric conversion element need not necessarily be placed at the position of the optical axis 43a of the lens but may be placed at a position excluding the optical axis 43a of the lens as long as light from the object of measurement is passed through the lens before being incident on and within the rear-side focal surface 43b.

As set forth above, according to the present invention, only the light reflected from a point on the object of measurement with the specific angular range is received by the specific area of the photoelectric conversion element installed on the focal surface in the rearward of the lens, whereby the characteristics of the reflection area on the object of measurement such as the reflectance, density, colors thereof and so forth can precisely be measured at all times despite the vertically fluctuating movement of the object of measurement.

Now, a description will be given in more detail of preferred embodiments of the invention with reference to the accompanying drawings.

A description will subsequently be given of an image forming apparatus embodying the present invention using an optical measuring method or an optical measuring apparatus according to the present invention first, and then of the optical measuring method and the optical measuring apparatus according to the present invention.

(Image Forming Apparatus Embodying the Present Invention)

Figure 18:
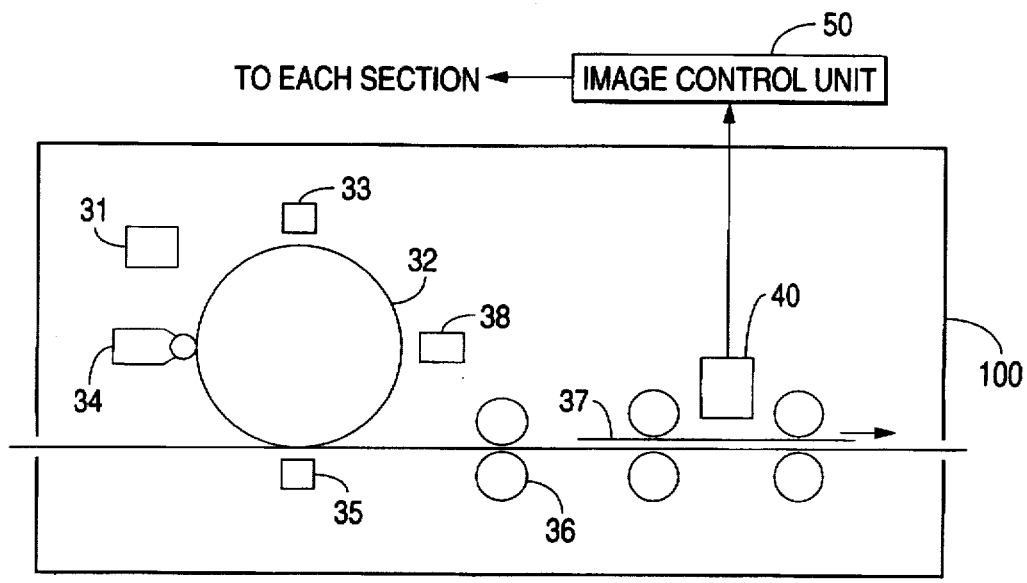
FIG. 18 is a diagram showing an example of an image forming apparatus using the optical measuring apparatus according to the present invention.

FIG. 18 shows the principal part of an exemplary image forming apparatus according to the present invention. This example of an image forming apparatus is used for forming an image on copying paper by electrophotography.

In an image input unit (not shown), an image on an original is read by a scanner so that input image data is obtained or the input image data created on an external computer is introduced into the apparatus. In an image processing unit (also not shown), the input image data from the image input unit is subjected to necessary processing such as color conversion and tone correction, whereby output image data to be output by an image output unit 100 is obtainable.

By a screen generator (not shown), the output image data from the image processing unit is converted into a laser on-off signal whose pulse width has been modulated in accordance with the pixel value. In the image output unit 100, the laser on-off signal is used to drive the laser diode of a laser output unit 31, and the laser beam modulated by the image signal is obtained from the image output unit 100, a photosensitive material 32 being irradiated with the laser beam.

The photosensitive material 32 is uniformly charged by a scolotron charger 33 and when it is radiated with the laser beam, an electrostatic latent image is formed on the photosensitive material 32. When the developing roll of a developing device 34 is brought into contact with the photosensitive material 32, the electrostatic latent image is developed into a toner image.

Further, the toner image on the photosensitive material 32 is transferred by a transfer device 35 onto paper 37 and the toner image on the paper 37 is fixed by a fixing device 36. The photosensitive material 32 is cleaned by a cleaner 38 after the toner image is transferred onto the paper 37. Thus, a first image-forming process is terminated.

In the image output unit 100, a banner sheet is output when the power supply of image forming apparatus is put to work and when the apparatus is manually set up by a user. The manual setting-up on the part of the user is made selectable by means of a mode changeover switch mounted on the user interface (not shown) of the image forming apparatus. When the mode changeover switch is used to select a manual set-up mode, the banner sheet is output immediately before the outputting of a document to be output by the user and the setting-up of the apparatus is carried out.

In the image output unit 100, further, an optical measuring apparatus 40, the construction of which is based on the above-described principle according to the present invention as will be described later, is installed backward from the fixing device 36. The optical measuring apparatus 40 is used for measuring the fixed image of a reference pattern called a patch for controlling image quality, the patch being formed on the banner sheet. The optical measuring apparatus 40 is designed to obtain information on the measured results including the reflectance measured by irradiating the paper 37 with light and receiving the light reflected therefrom; density, color and the like based on the reflectance.

The information obtained by the optical measuring apparatus 40 from the measured results is sent to an image control unit 50. According to the measured results in the optical measuring apparatus 40, the image control unit 50 controls the laser output unit 31, the scolotron charger 33 or the developing device 34 in the image output unit 100 so as to control the quality of an output image.

Figure 19:
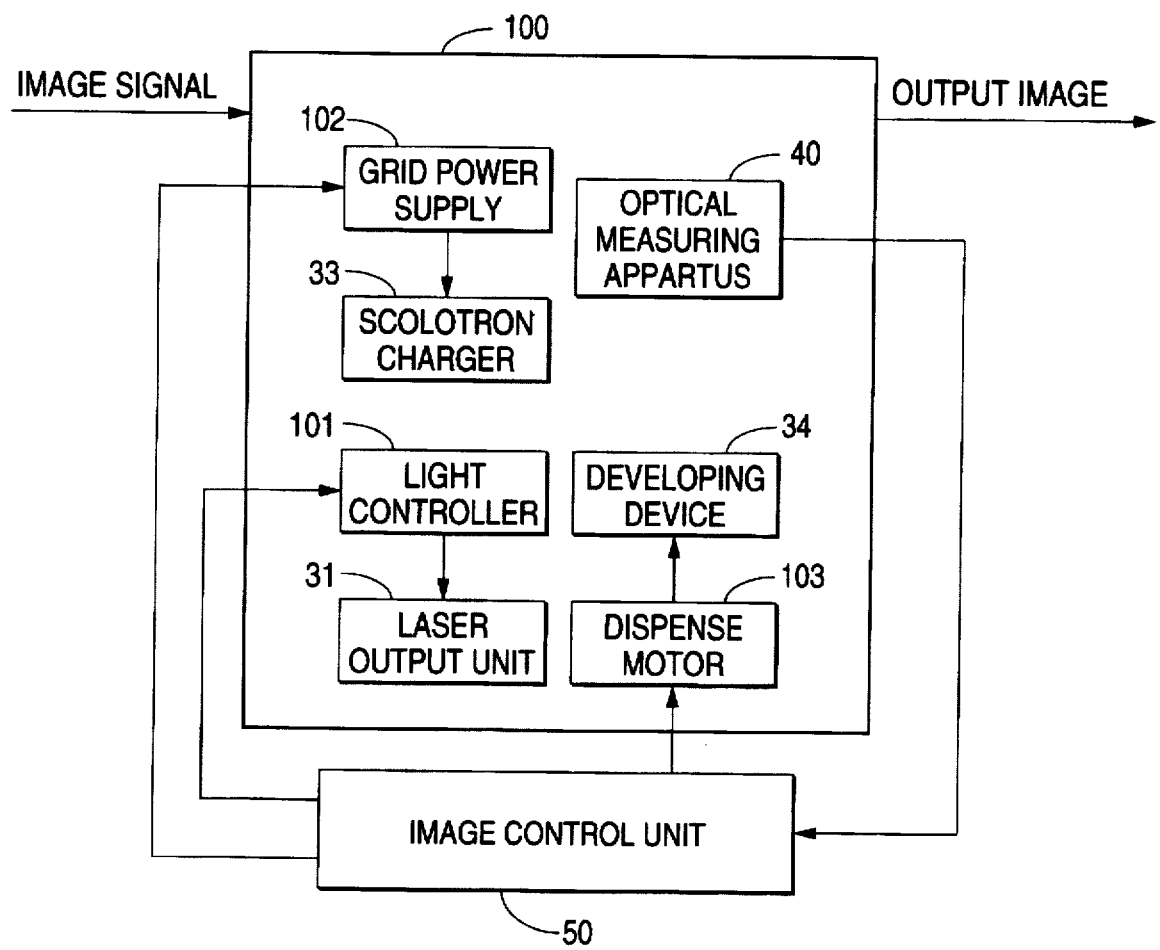
FIG. 19 is a diagram showing a portion for use in controlling image quality in the image forming apparatus of FIG. 18.
Figure 20:
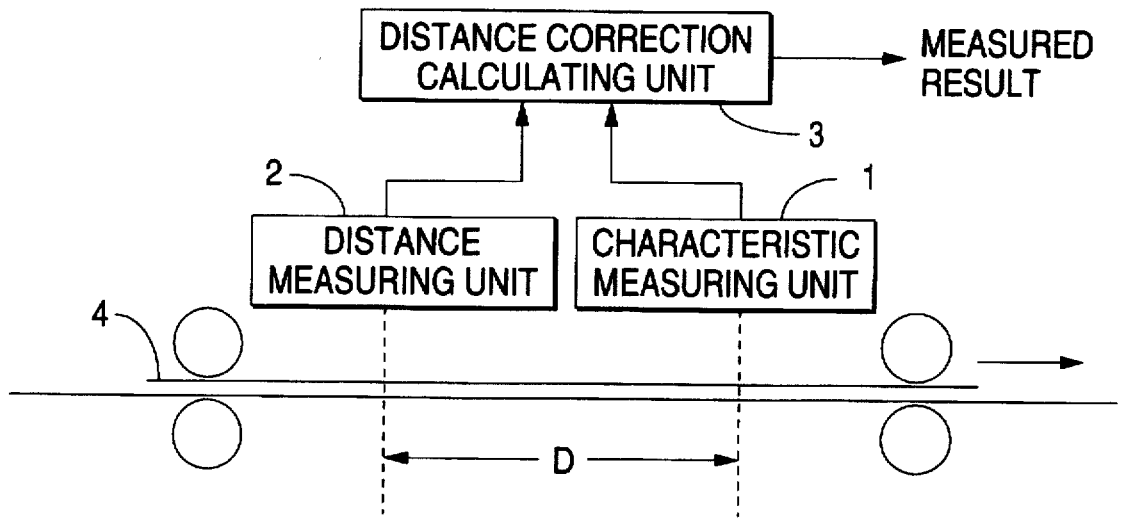
FIG. 20 is a diagram showing an example of a conventional image forming apparatus.
Figure 21:
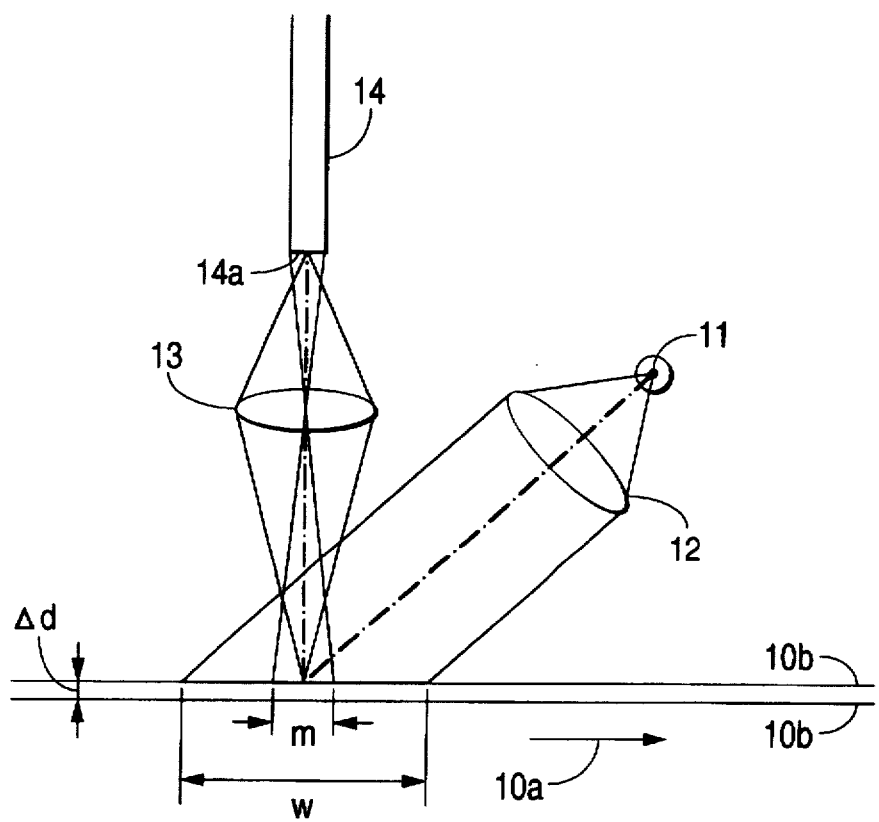
FIG. 21 is a diagram showing another example of a conventional image forming apparatus.

FIG. 19 shows the principal parts of the image output unit 100 of the image forming apparatus with the attention substantially directed to image control according to this embodiment of the invention. The image output unit 100 includes a quantity-of-light controller 101, a grid power supply 102 for the scolotron charger 33, a dispense motor 103 for controlling the supply of toner to the developing device 34 and the like.

On the basis of the measured results in the optical measuring apparatus 40, that is, measurement outputs such as the density of the fixed image with the reference pattern in the optical measuring apparatus 40, the image control unit 50 controls the quantity of operation of the image output unit 100; more specifically, the image control unit 50 controls the grid voltage of the scolotron charger 33 and the laser output power of the laser output unit 31 so as to control the quality of the output image. On the basis of the measured results in the optical measuring apparatus 40, further, the image control unit 50 drives the dispense motor 103 to control the quality of the output image by controlling the supplementary quantity of toner supplied to the developing device 34 in order to control the developing image density.

Incidentally, the image control unit 50 may be so arranged as to control parameters dealing with image quality in the transfer device 35 and the fixing device 36.

As set forth above, in an image forming apparatus embodying the present invention, the measured results in the optical measuring apparatus 40 are fed back to the image control unit 50, and each of the component parts such as the laser output unit 31 and the scolotron charger 33 of the image output unit 100 is controlled by the image control unit 50, whereby the quality of the output image is made controllable. The paper 37 at this time is kept moving while the movement of its surface is fluctuating in a vertical direction perpendicular to the direction in which the paper is conveyed. However, precise measurement is carried out without being affected by the vertically fluctuating movement of the surface of the paper in the optical measuring apparatus 40.

(Optical Measuring Method and Apparatus Embodying the Present Invention)

Figure 1:
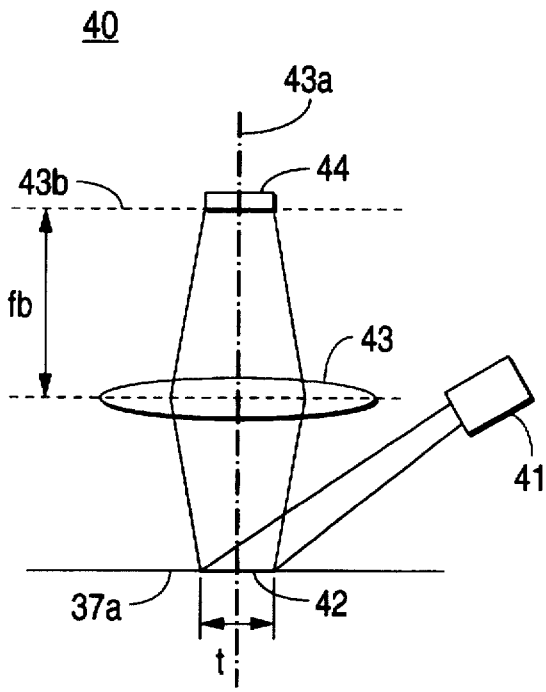
FIG. 1 is a diagram showing an optical measuring apparatus embodying the present invention.
Figure 2:
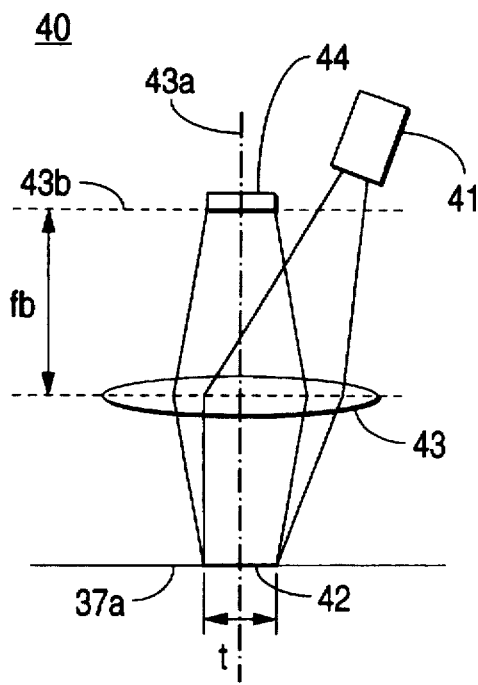
FIG. 2 is a diagram showing another optical measuring apparatus embodying the present invention.

FIGS. 1–2 shows the basic construction of the optical measuring apparatus 40 according to the present invention, wherein FIG. 1 refers to a case where the paper surface 37a is irradiated with light from a light source 41 not via a lens 43, whereas FIG. 2 refers to a case where the paper surface 37a as an object of measurement is irradiated with the light from the light source 41 via the lens 43.

The optical measuring apparatus 40 is substantially constituted of the light source 41 for emitting light into a reflection area 42 on the paper surface 37a as will be described later, the lens 43 for converging the light reflected from the reflection area 42, and a photoelectric conversion element 44 which is installed on a focal surface 43b in the rearward of the lens 43.

The light reception area of the photoelectric conversion element 44 is caused to be contained in the focal surface 43b and set specifically large enough to receive part of the light passed through the lens 43. The size of the light reception area is what results from taking into consideration frequency response as a light reception output and set relatively smaller.

With this arrangement as described above, only light in the predetermined angular range determined by the light reception area of the photoelectric conversion element 44 out of the light reflected from the paper surface 37a is received by the photoelectric conversion element 44. Further, the total quantity of light received by the photoelectric conversion element 44 is made the output of the photoelectric conversion element 44. Although not shown in FIGS. 1–2, the optical measuring apparatus 40 has an analytical unit for analyzing the light reception output in order to gain various measured results from the reflectance, for example.

The light emitted from the light source 41 is desired to be close to parallel rays of light but may be those other than such parallel rays of light. According to the present invention, an LED is employed as the light source 41, and so are a flat convex lens and a PIN-Si photodiode as the lens 43 and the photoelectric conversion element 44, respectively.

Although the width of the lens 43 is assumed to be infinite in the theoretic description of FIG. 3, the width of a lens is actually finite and the width thereof has to be taken into consideration. For this reason, the light from the light source 41 needs to be emitted into the reflection area 42 so as to meet the following limiting conditions in its relation to the width of the lens.

Figure 4:
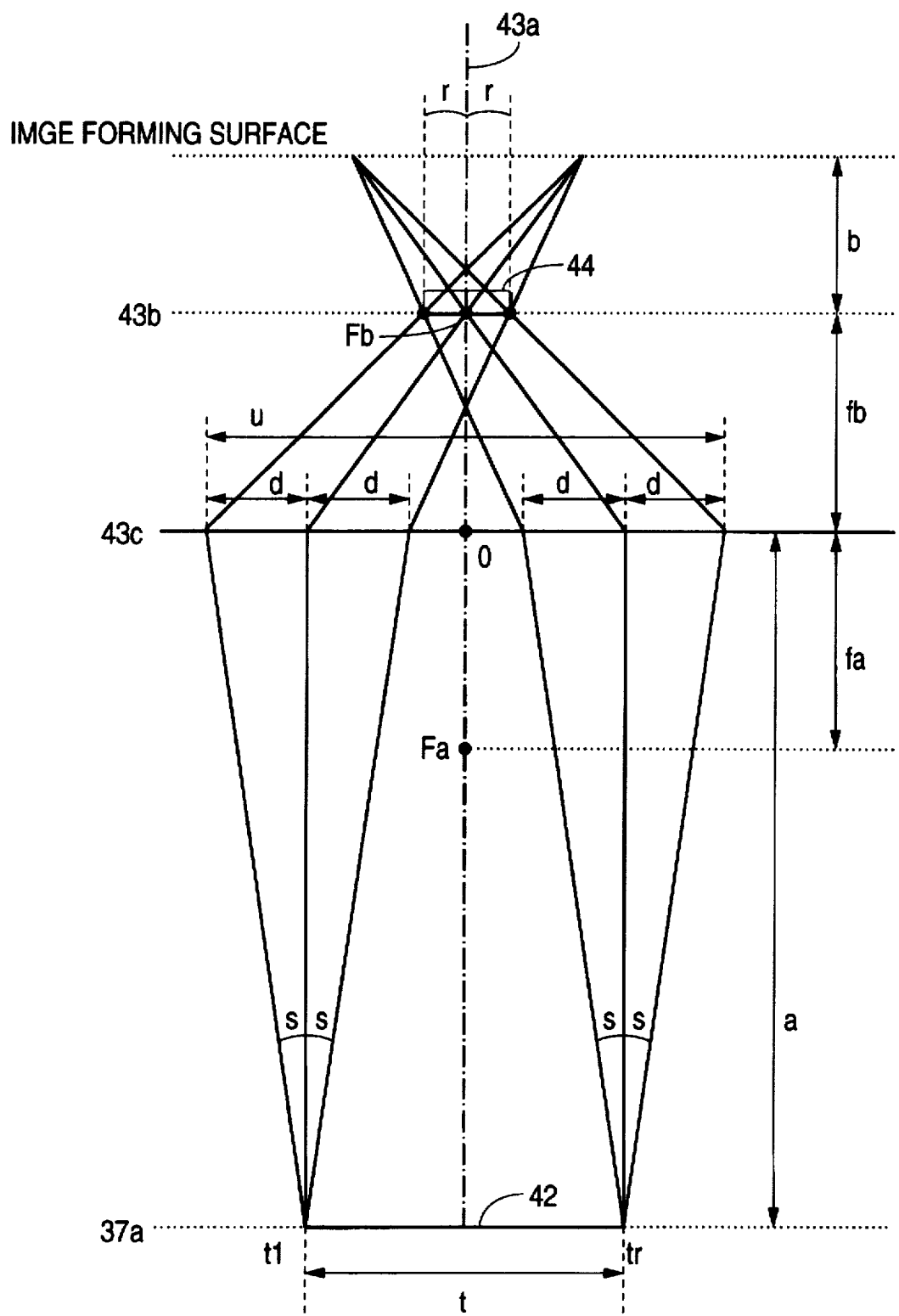
FIG. 4 is a diagram illustrating requirements in the optical measuring method according to the present invention.

As shown in FIG. 4, the rays of light reflected from points within the reflection area 42 on the paper surface 37a and incident on the photoelectric conversion element 44 are reflected from the respective points in the range of angles s, that is, in the range of angles s×2 on both sides in a direction parallel to the optical axis 43a and caused to expand to a width of d×2 over the lens 43 according to the aforementioned Eqs. (5), (6).

As is obvious from FIG. 4, in order that the rays of light reflected from the ends t1, tr of the reflection area 42 may be passed within the width u of the lens 43 before being incident on the photoelectric conversion element 44, $$u \geq 5 + 2 \cdot d \qquad (12)$$

must be satisfied.
Where $$d = a \cdot \tan(s) \qquad (13)$$

and since $$\tan(s) = r/fa \qquad (14)$$

from the aforementioned Eqs. (9), (10), Eq. (12) becomes $$u \geq t + 2 \cdot a \cdot r/fa \qquad (15)$$

Since the width u of the lens, the width 2r of the photoelectric conversion element 44 and the focal length fa are fixed values, there exists no light which is caused not to pass the lens 43 out of what should be incident on the photoelectric conversion element 44 on condition that the width t of the reflection area 42 and the distance a between the lens 43 and the paper surface 37a in connection with the irradiation of the paper surface 37a with light and the reflection of light from the paper surface 37a are within a range satisfying the limiting conditions of Eq. (15).

Therefore, the light emitted into the reflection area 42 satisfying the limiting conditions of Eq. (15) and reflected within the angular range of s×2 are passed through the lens 43 and then incident on the photoelectric conversion element 44. Despite the vertically fluctuating movement of the paper surface 37a, the theoretical output change is reduced to zero, so that extremely precise measurement becomes possible.

Figure 5:
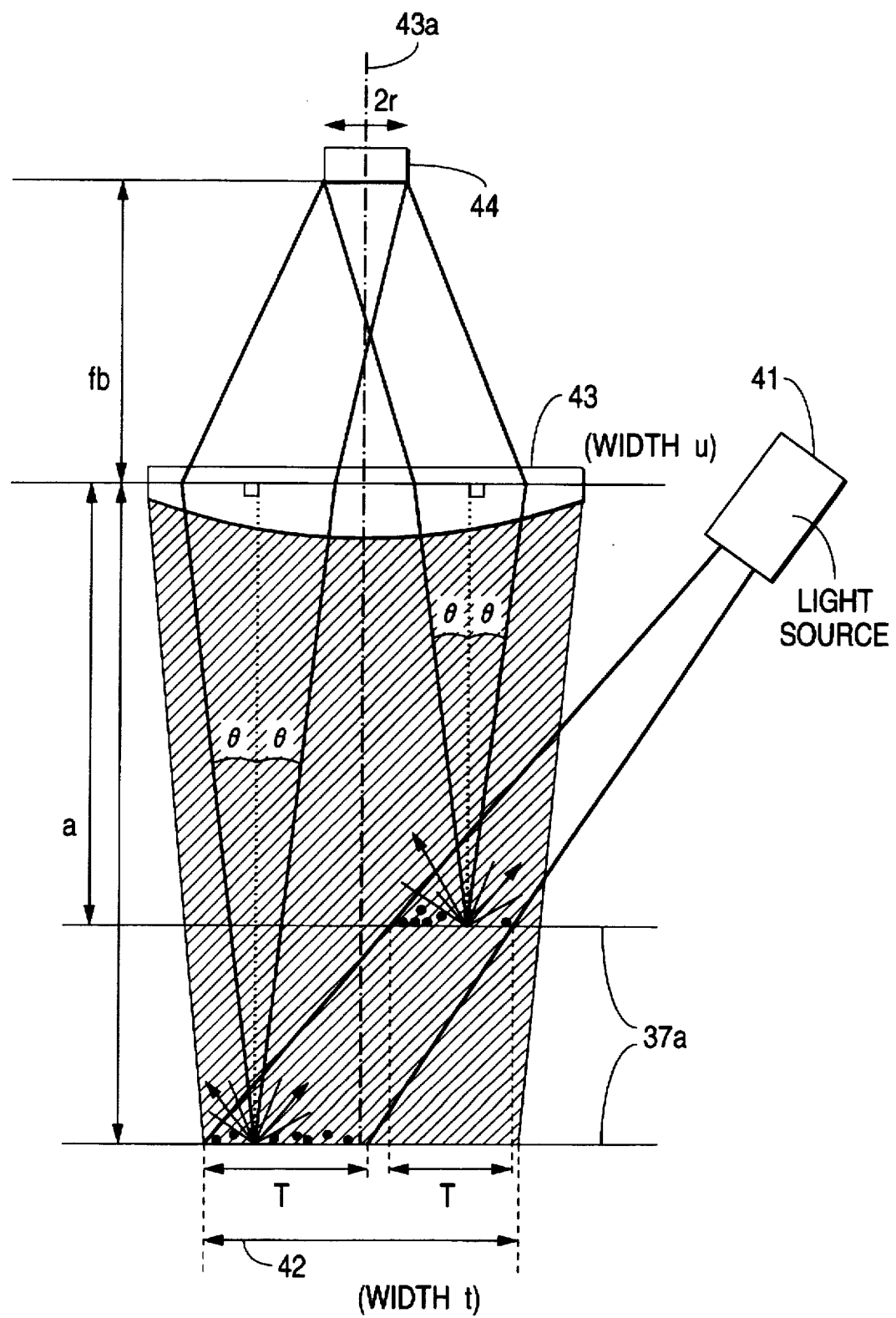
FIG. 5 is a diagram illustrating requirements in the optical measuring method according to the present invention.

As shown in FIG. 5 of this example, an irradiation area T is set in such a manner that the irradiation area T on the paper surface 37a by means of the light source 41 is always within the aforementioned reflection area 42. Consequently, the photoelectric conversion element 44 is allowed to receive the light reflected from the paper surface 37a via the lens 43 without being affected by the vertically fluctuating movement of the paper surface 37a, if any.

Incidentally, the irradiation area T is made smaller than the unit patch of the reference pattern for use in controlling image quality. This is because when the irradiation area T is greater than the unit patch, the light reflected from a blank portion around the patch affects the measured results.

As shown in FIGS. 4–5, though the reflection area 42 and the photoelectric conversion element 44 have the same length on both sides of the optical axis 43a, the length on one side may be set different from that on the other. In this case, the angular range of light incident on the photoelectric conversion element 44 from each point within the reflection area 42 results in differing from that range on the other side with respect to the parallel direction of the optical axis 43a.

As described above, moreover, the position where the photoelectric conversion element 44 is installed needs not what contains the optical axis 43a of the lens 43 as long as the photoelectric conversion element 44 is contained in the focal surface 43b in the rearward of the lens 43. In this case, as shown in FIGS. 4–5, the angular range of light incident on the photoelectric conversion element 44 from each point within the reflection area 42 exists on one side with respect to the parallel direction of the optical axis 43a.

As described above, further, the distance from the optical axis 43a to the end of the photoelectric conversion element 44 needs not to be constant because an actual optical system is considered to be a rotary body centering around the optical axis 43a of the lens 43. The shape of the photoelectric conversion element 44 may be what is desired; for example, circular, square or the like. At this time, the following is generally established:

$$u/2 \geq t/2 + a \cdot t/fa \tag{16}$$

Thus, the limiting conditions according to the present invention include setting the reflection area 42 which is dependent on the specifications of the lens 43 and the photoelectric conversion element 44; however, the limiting conditions are free from being affecting by any other conditions, for example, characteristics such as whether light from the light source 41 is diffusion light or parallel light, whether the quantity-of-light distribution is uniform or the like.

However, as long as a tolerance originating from the quantity of fluctuating movement of an object of measurement stays in a range less than the tolerance that a person in charge of measurement demands even in a case where by irradiating an area not under the aforementioned limiting conditions with light, the area is measured as a reflection area, the characteristics of the object of measurement can be measured satisfactorily.

When the photoelectric conversion element 44 is installed in the focal surface 43b in the rearward of the lens 43, the following procedure is followed. When, for example, a blank sheet of paper whose paper surface 37a is in a uniform white state is irradiated with light and then moved within a plane perpendicular to the optical axis 43a of the lens 43 simultaneously when the photoelectric conversion element 44 is moved within a plane perpendicular to the optical axis 43a, a planar position is searched in that the light-reception output levels are equalized in any position within the plane, and the photoelectric conversion element 44 is installed in a desired position in the planar position.

In the case where the paper surface 37a is irradiated with light from the light source 41 not via the lens 43 as shown in FIG. 1, the use of a flat convex lens having a width (diameter) u of 15 mm as the lens 43 with a focal distance f (=fa=fb) of 20 mm, a PIN-si photodiode having a diameter 2r of 1.2 mm as the photoelectric conversion element 44 whose center position is made to conform to the optical axis 43a of the lens 43, and an LED as the light source 41 as described above has made attainable a small-sized optical measuring apparatus 30 mm×30 mm×20 mm on the whole.

In this specific example with the limiting conditions of the reflection area 42, since there are used the lens 43 having a diameter u of 15 mm, the photoelectric conversion element 44 having a diameter 2r of 1.2 mm and the lens 43 having a focal distance fa of 20 mm, the diameter t of the reflection area 42 is possible up to 13.8 mm when the distance a between the paper surface and the lens is 20 mm.

When a very small area is measured, it is possible to measure an area whose diameter t is about 1 mm or smaller and to evaluate the measured results by reducing the aforementioned values as there are.

Figure 6:
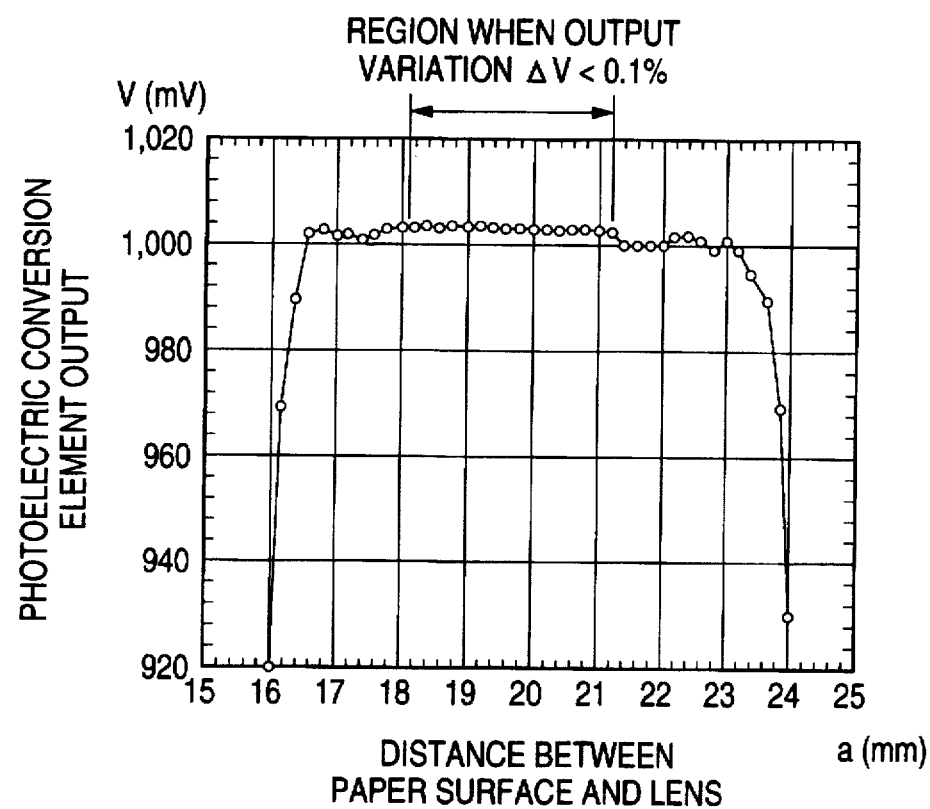
FIG. 6 is a graph showing specific characteristics of the optical measuring apparatus in the example of FIG. 1.

FIG. 6 refers to a case where the optical measuring apparatus according to this embodiment of the invention is used for measuring purposes and shows variation in light reception output when the movement of the paper surface fluctuates. As is obvious from FIG. 6, according to this embodiment of the invention, the variation of the light reception output can be suppressed to 1% or lower even when the fluctuating movement of the paper surface is 1 mm or greater, so that precise measurement is made possible to the extent that an error such as an aberration of the lens 43 and the like originating from each of the component parts remains. As described above, because variation of light reception output reaches about 15% when the vertically fluctuating movement of the paper surface 37a is 1 mm in a case where the method or apparatus according to the present invention is not relied upon, it is feasible to increase the precision greatly, for example, by two digits or greater according to the aforementioned embodiment of the invention.

In this example, further, the optical measuring apparatus body can be produced at the cost of as extremely low as about ¥1,000.- since the price of each component parts ranges from several ¥10 to several ¥100.

In the case where the paper surface 37a is irradiated with light from the light source 41 via the lens 43 as shown in FIG. 2, the use of a flat convex lens having a width (diameter) u of 20 mm as the lens 43 with a focal distance f (=fa=fb) of 30 mm, a PIN-si photodiode having a diameter 2r of 1.2 mm as the photoelectric conversion element 44 whose center position is made to conform to the optical axis 43a of the lens 43, and an LED as the light source 41 as described above has made attainable a small-sized optical measuring apparatus 30 mm×30 mm×40 mm on the whole.

As far as the specific limiting conditions of the reflection area 42 are concerned according to this embodiment of the invention, the diameter t of the reflection area 42 can be up to 19.2 mm from Eq. (15) when the distance a between the paper surface and the lens since the diameter u of the lens 43 is 20 mm; the diameter 2r of the photoelectric conversion element 44 is 1.2 mm; and the focal length fa of the lens 43 is 30 mm.

Even in this case where a very small area is measured, these numerical values are directly scaled down, whereby an area whose diameter t is about 1 mm or smaller can be measured and evaluated.

Figure 7:
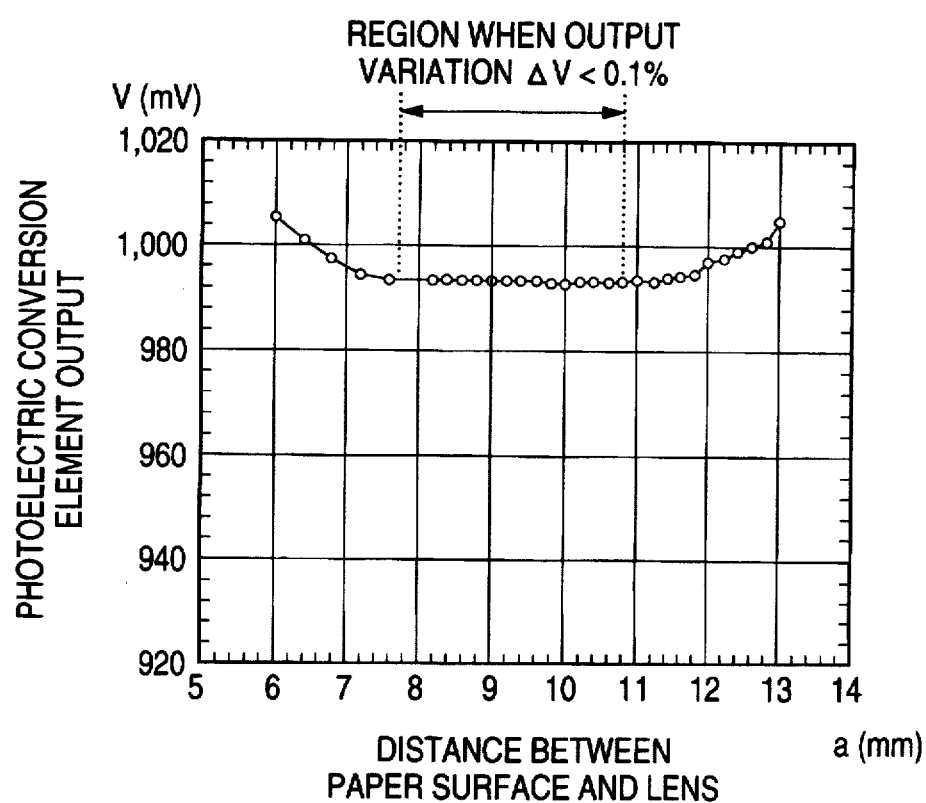
FIG. 7 is a graph showing specific characteristics of the optical measuring apparatus in the example of FIG. 2.

FIG. 7 shows variation of the light reception output when the specific optical measuring apparatus according to this embodiment of the invention is used to measure while the movement of the focal surface is fluctuating. As is obvious from FIG. 7, according to this embodiment of the invention, the variation of the light reception output can be suppressed to 0.1% or lower even when the vertically fluctuating movement of the paper surface is 1 mm or greater, so that precise measurement becomes possible to the extent that an error such as an aberration of the lens 43 and the like originating from each of the component parts remains. As described above, because variation of light reception output reaches about 15% when the vertically fluctuating movement of the paper surface 37a is 1 mm in a case where the method or apparatus according to the present invention is not relied upon, it is feasible to increase the precision greatly, for example, by two digits or greater according to the aforementioned embodiment of the invention.

Even in this example, further, the optical measuring apparatus body can be produced at the cost of as extremely low as about ¥1,000.- since the price of each component parts ranges from several ¥10 to several ¥100.

Now, a comparison is made between cases where the paper surface 37a is irradiated with light from the light source 41 not via the lens 43 as shown in FIG. 1 and where the paper surface 37a is irradiated with light from the light source 41 via the lens 43 as shown in FIG. 2.

Figure 8A:
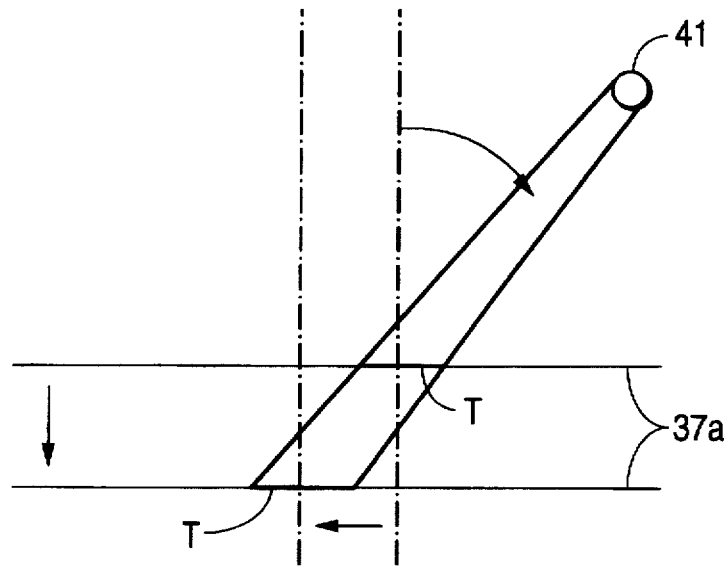
FIGS. 8A and 8B are diagrams illustration a comparison between the optical measuring apparatus in the example of FIG. 1 and the optical measuring apparatus in the example of FIG. 2.

As shown in FIG. 1, light from the light source 41 is caused to be incident on the paper surface 37a at a large angle with respect to the optical axis 43a of the lens 43 since the light source 41 is situated on the side of the lens 43 when the paper surface 37a is irradiated with the light from the light source 41 not via the lens 43. For this reason, as shown in FIG. 8(A), the irradiation area T on the paper surface 37a is caused to greatly move horizontally (in a direction perpendicular to the optical axis 43a) because of the light source 41 when the movement of the paper surface 37a vertically fluctuates.

Figure 8B:
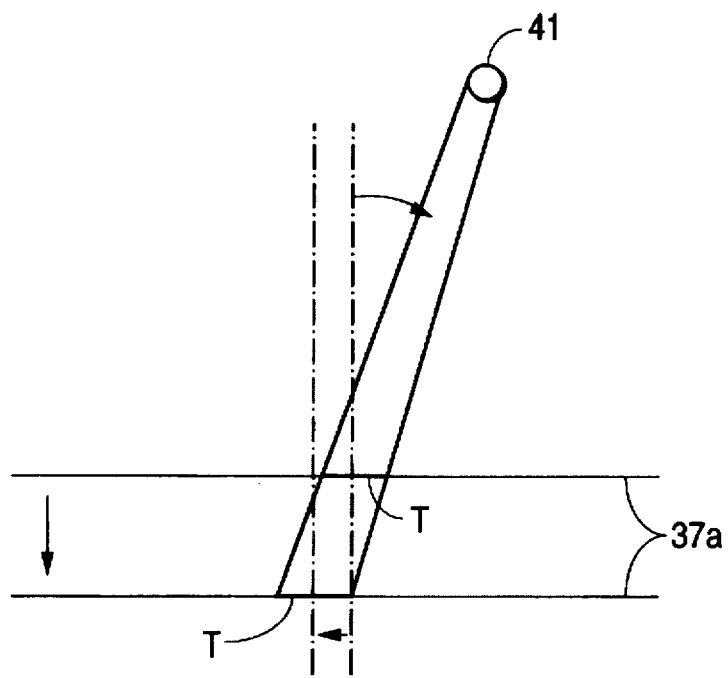

As shown in FIG. 2, on the other hand, light from the light source 41 is caused to be incident on the paper surface 37a at a smaller angle with respect to the optical axis 43a of the lens 43 when the paper surface 37a is irradiated with the light from the light source 41 via the lens 43. For this reason, as shown in FIG. 8(B), the irradiation area T on the paper surface 37a is caused to less move horizontally because of the light source 41 when the movement of the paper surface 37a vertically fluctuates to the same extent.

When the paper surface 37a is irradiated with light from the light source 41 not via the lens 43 and consequently when the movement of the paper surface 37a vertically fluctuates, the light passed through the peripheral portion of the lens 43 out of the light reflected from the irradiation area T on the paper surface 37a increases and the quantity of the light received by the photoelectric conversion element 44 varies because of spherical aberration that the lens 43 possesses. Therefore, the light reception output greatly varies with the vertically fluctuating movement of the paper surface in comparison with the irradiation of the paper surface 37a with light from the light source 41 via the lens 43.

When it is attempted to make light from the light source 41 incident on the paper surface 37a at a smaller angle with respect to the optical axis 43a by decreasing the width (diameter) u of the lens 43 and bringing the light source 41 closer to the optical axis 43a in order to reduce the variation of the light reception output to the same extent that the paper surface 37a is irradiated via the lens 43 at the time the paper surface 37a is irradiated with the light from the light source 41 not via the lens 43, the limiting conditions expressed by Eq. (15) become hardly satisfied.

When it is thus attempted to make light from the light source 41 incident on the paper surface 37a at a smaller angle with respect to the optical axis 43a by keeping the lens 43 at a distance, the whole optical measuring apparatus becomes larger in size in a direction perpendicular to the paper surface 37a. When it is attempted to make light from the light source 41 incident on the paper surface 37a at a smaller angle with respect to the optical axis 43a by not putting the light source 41 in the lateral direction of the lens 43 but putting it between the lens 43 and the paper surface 37a, further, the light reflected from the paper surface 37a is hidden by the light source 41 and this renders the measurement difficult.

In those respects, the case of irradiating the paper surface 37a with light from the light source 41 via the lens 43 as shown in FIG. 2 is preferable to the case of irradiating the paper surface 37a with light from the light source 41 not via the lens 43 as shown in FIG. 1. Even when the paper surface 37a is irradiated with light from the light source 41 not via the lens 43 as stated above, however, the variation of the light reception output due to the vertically fluctuating movement of the paper surface 37a can be suppressed satisfactorily.

When the paper surface 37a is irradiated with light from the light source 41 via the lens 43 as shown in FIG. 2, the light source 41 is, as shown therein, preferably placed backward from the focal surface 43b in the rearward of the lens 43. As the rays of light generated from the light source 41 are converged when they pass through the lens 43 with the placement of the light source 41 farther from the lens 43 than the focal surface 43b in the rearward of the lens 43, the reflection area 42 on the paper surface 37a can certainly be limited to the condition of Eq. (15).

When the light source 41 is placed closer to the lens 43 than the rear-side focal surface 43b, on the contrary, the rays of light from the light source 41 are passed through the lens 43 and then caused to expand, whereby the reflection area 42 becomes hardly limited to the condition of Eq. (15). When the light source 41 is placed on the rear-side focal surface 43b, the rays of light from the light source 41 are passed through the lens 43 and then become substantially parallel rays of light, whereby the reflection area 42 becomes also hardly limited to the condition of Eq. (15) because the reflection area 42 becomes equal in size to the width (diameter) of the lens 43.

When the paper surface 37a is irradiated with light from the light source 41 not via the lens 43 as shown in FIG. 1, the reflection area 42 is actually limited and it is needed to narrow the passage of the light from the light source 41 by providing the light source 41 with a diaphragm.

When the paper surface 37a is irradiated with light from the light source 41 via the lens 43, the light source 41 may be placed closer to the lens 43 than the rear-side focal surface 43b or on the focal surface 43b, on condition that the passage of the light from the light source 41 is sufficiently narrowed by providing the light source 41 with such a diaphragm.

(Another Optical Measuring Method and Apparatus Embodying the Present Invention)

(A case where an opening or a condenser lens is installed)

FIG. 1 or 2 refers to the case where the photoelectric conversion element 44 is disposed on the focal surface 43b in the rearward of the lens 43. However, the photoelectric conversion element 44 is not necessarily be placed on the rear-side focal surface 43b but may be disposed backward from the rear-side focal surface 43b as long as the light reflected from the paper surface 37a within a specific angular range and then incident on solely the specific area of the rear-side focal surface 43b is theoretically and totally made receivable by the photoelectric conversion element 44.

Figure 9:
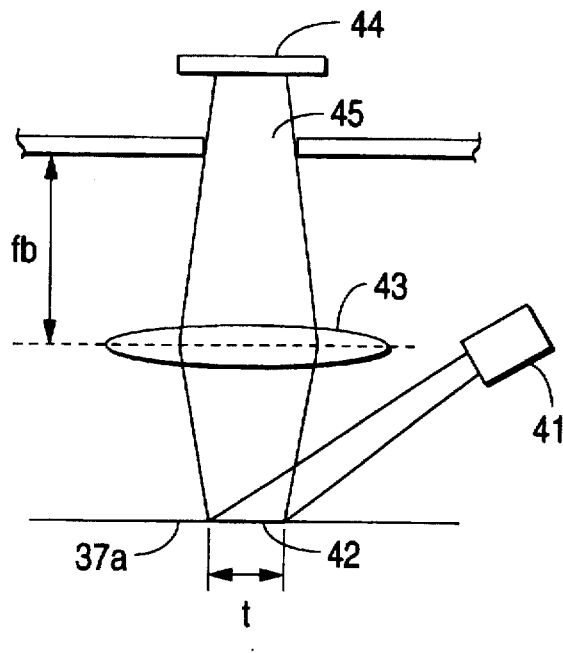
FIG. 9 is a diagram showing still another optical measuring apparatus embodying the present invention.
Figure 10:
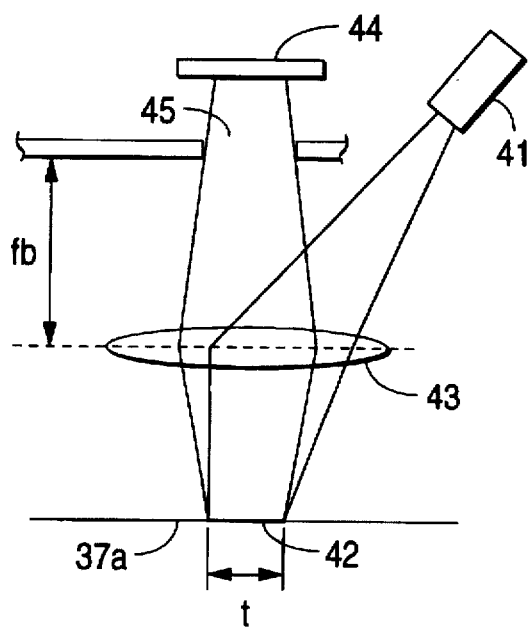
FIG. 10 is a diagram showing still another optical measuring apparatus embodying the present invention.

FIGS. 9 or 10 refers to an example in which the photoelectric conversion element 44 is placed backward from the rear-side focal surface, and an opening 45 is provided in the position of the specific area of the rear-side focal surface, whereby only light passed through the opening 45 is totally received by the photoelectric conversion element 44 installed in the rear of the opening 45.

FIG. 9 refers to a case where the paper surface 37a is irradiated with light from the light source 41 not via the lens 43, whereas FIG. 10 refers to a case where the paper surface 37a is irradiated with light from the light source 41 via the lens 43.

In this example, the light reflected from the paper surface 37a within a specific angular range and then incident on solely the specific area of the rear-side focal surface 43b is totally passed through the opening 45 before being received by the photoelectric conversion element 44. Consequently, like the examples shown in FIGS. 1 or 2, the light reception output unaffected by the vertically fluctuating movement of the paper surface 37a is obtainable from the photoelectric conversion element 44.

In this example, further, it is only needed to set the size of the opening 45 to the length 2r shown in FIGS. 4–5 and the size of the photoelectric conversion element 44 may be selected optionally as long as the only light passed through the opening 45 is made receivable.

Figure 11:
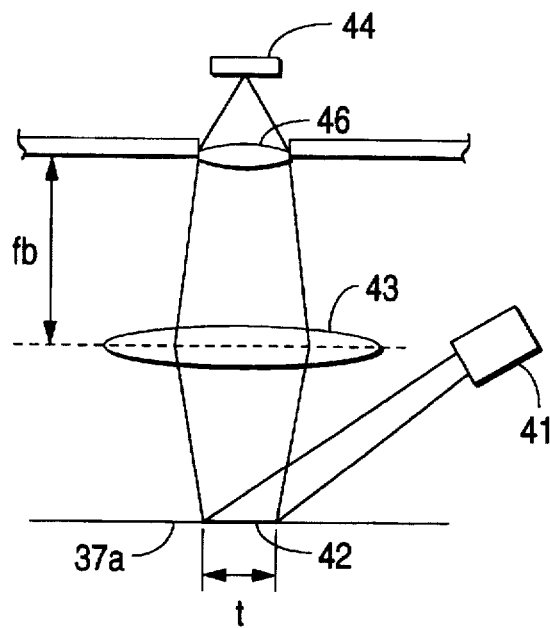
FIG. 11 is a diagram showing still another optical measuring apparatus embodying the present invention.
Figure 12:
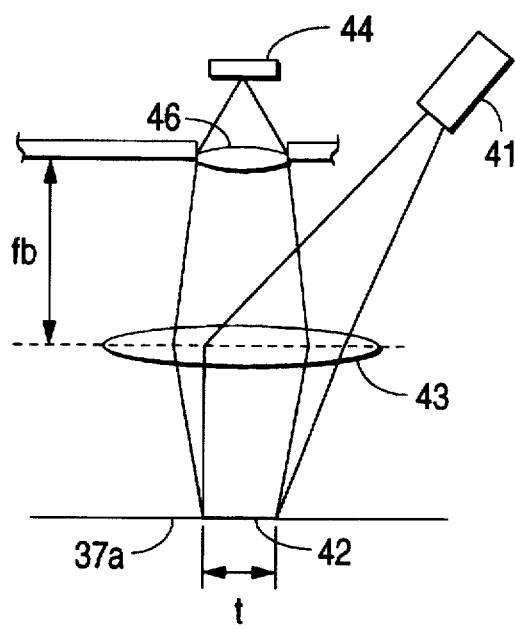
FIG. 12 is a diagram showing still another optical measuring apparatus embodying the present invention.

FIGS. 11 or 12 refers to a case where a condenser lens 46 is installed in the position of the opening 45 according to the embodiment of the invention shown in FIGS. 9 or 10, that is, in the position of the specific area of the focal surface in the rearward of the lens 43, and only the light converged by the condenser lens 46 is received by the photoelectric conversion element 44 installed in the rearward of the condenser lens 46.

Incidentally, FIG. 11 refers to a case where the paper surface 37a is irradiated with light from the light source 41 not via the lens 43, whereby FIG. 12 refers to a case where the paper surface 37a is irradiated with light from the light source 41 via the lens 43.

Since only the whole light reflected from the paper surface 37a within the specific angular range and incident on the specific area of the rear-side focal surface is focused by the condenser lens 46 before being received by the photoelectric conversion element 44 even in this example, like the examples shown in FIGS. 1 or 2, the light reception output unaffected by the vertically fluctuating movement of the paper surface 37a is obtainable from the photoelectric conversion element 44.

(Measurement of Colors of Image)

When colors of an image are measured, there is employed a method of irradiating a paper surface having an image formed thereon with light from an angle of 45° in a direction perpendicular to the paper surface and receiving the light from an angle of 0° or conversely irradiating the paper surface with light from an angle of 0° and receiving the light from an angle of 45°.

When colors are measured as shown in FIGS. 1 or 2 according to the present invention by irradiating the paper surface 37a with light from the light source 41 not via or via the lens 43, the paper surface 37a is irradiated with light from the light source 41 at an angle of 45° with respect to the optical axis 43a of the lens 43. However, the paper surface 37a may be irradiated with light at an angle of 60° or smaller with respect to the optical axis 43a unless the deviation of the paper surface 37a in the direction of diffusion is greater.

In the examples with reference to FIGS. 1, 2, 9, 10, 11 or 12, the density of an image of cyan, magenta or yellow as a complementary red, green or blue color formed on the paper surface 37a can be measured from the light reception output of the photoelectric conversion element 44 by the use of the light source 41 capable of emitting red, green or blue color light. For the measurement of the density of a black image, use can be made of a light source for emitting red, green or blue color light or white light.

In the optical measuring apparatus shown in the aforementioned example, the light source 41 for emitting red, green or blue color light was used to measure the density of an image of cyan, magenta or yellow on the paper surface 37a. Then the variation of the light reception output could be suppressed to 0.1% or lower even when the vertically fluctuating movement of the paper surface 37a was 1 mm or greater; this is equivalent to a level at which a discrimination between 0.1 or lower and about 0.4 can be made in accordance with the density as far as aberration is concerned. In other words, the discrimination can readily be made up to a level of aberration at which the naked eye is impossible to do.

Further, colors of a full-color image may be evaluated by providing a plurality of light sources such as those emitting red, green and blue color light and sequentially lighting the plurality of light sources.

Figure 13:
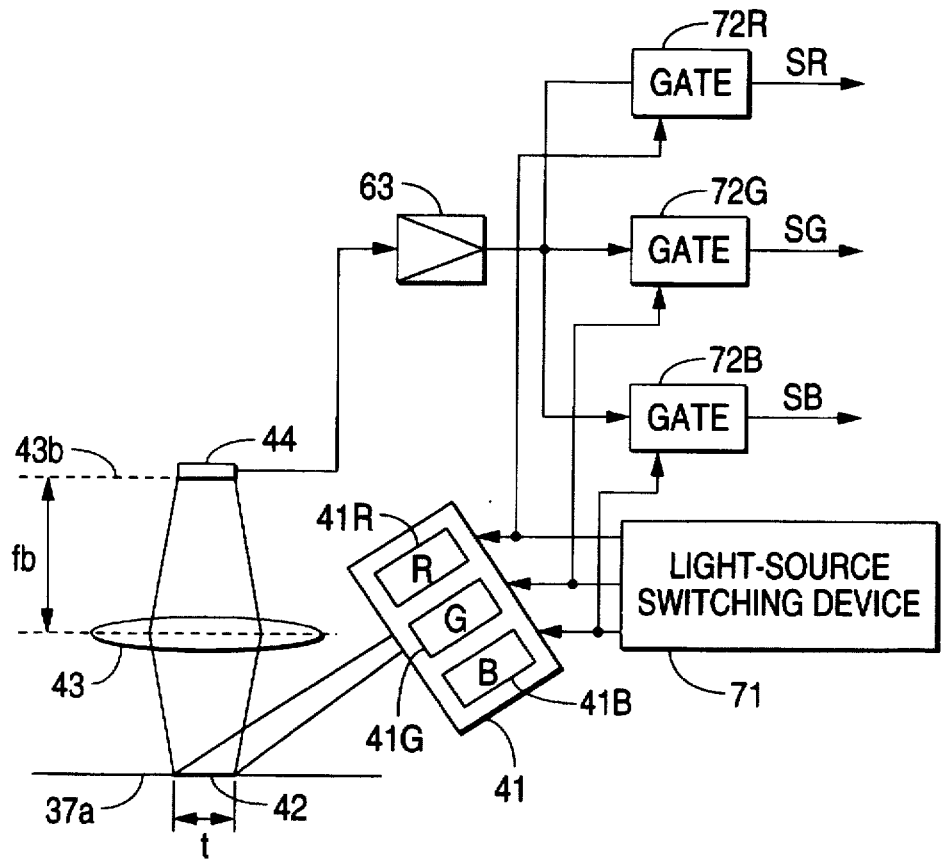
FIG. 13 is a diagram showing still another optical measuring apparatus embodying the present invention.

FIG. 13 shows an example in the above case. Patch images of cyan, magenta and yellow as complementary red, green, blue colors are formed in order on the paper surface 37a in the direction of movement and three light sources 41R, 41G, 41B for emitting red, green and blue color light are respectively arranged as light sources 41 at intervals of 120° as viewed from the direction of the optical axis of the lens 43, for example.

These light sources 41R, 41G, 41B are switched over by a light-source switching device 71 in synchronization with the cyan, magenta and yellow images on the paper surface 37a and by supplying the light reception output of the photoelectric conversion element 44 via an amplifier 63 to gate circuits 72R, 72G, 72B, the gates are opened for a period during which the respective light sources 41R, 41G, 41B are lighted in synchronization with switching signals from the light-source switching device 71. The light reception outputs SR, SG, SB of the photoelectric conversion element 44 are then taken out from the gate circuits 72R, 72G, 72B for a period during which the respective light sources 41R, 41G, 41B are lighted and the light reception outputs SR, SG, SB are supplied to a measurement computing unit (not shown).

Consequently, the density of the images of cyan, magenta and yellow on the paper surface 37a can be measured with the outputs SR, SG, SB of the gate circuits 72R, 72G, 72B and further the colors of the full-color image can also be evaluated by comprehensively calculating the outputs SR, SG, SB in the measurement computing unit.

When the black patch image is also formed on the paper surface 37a, any one of the light sources 41R, 41G, 41B is simultaneously used for measuring the black image or a light source for emitting white light is added so as to measure the black image, and a gate circuit for taking out the measurement output of the black image from the light reception output of the photoelectric conversion element 44 is additionally installed.

Although FIG. 13 refers to the case where the paper surface 37a is irradiated with light from the light source 41 not via the lens 43, the arrangement shown in FIG. 13 is applicable likewise to even the case where the paper surface 37a is irradiated with light from the light source 41 via the lens 43.

Figure 14:
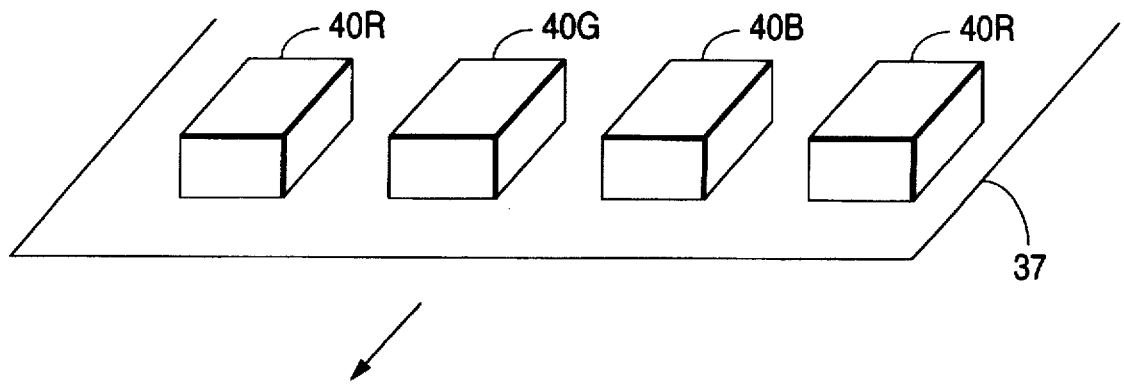
FIG. 14 is a diagram showing an example of an optical measuring system according to the present invention.

FIG. 14 shows another example of measuring image colors, wherein cyan, magenta, yellow and black patch images are formed on the paper surface 37a in a lateral direction perpendicular to the conveying direction as shown by an arrow.

As an optical measuring system, four optical measuring apparatus 40R, 40G, 40B and 40R respectively using the aforementioned light sources 41 for emitting red, green, blue and red color light, the lenses 43 and the photoelectric conversion elements 44 are arranged in a lateral direction perpendicular to the conveying direction, so that the density of cyan, magenta, yellow and black images on the paper surface 37a is measured by the optical measuring apparatus 40R, 40G, 40B and 40R.

Consequently, colors of a full-color image can be evaluated by comprehensively calculating the measured outputs of the optical measuring apparatus 40R, 40G, 40B and 40R and by feeding back the measured results to each process step in the image forming apparatus, an image of good quality is obtainable therein.

Figure 15:
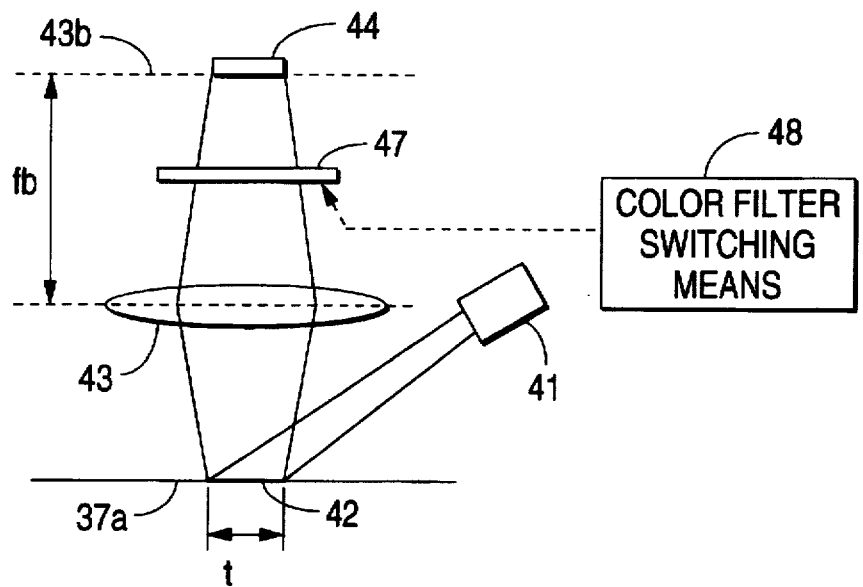
FIG. 15 is a diagram showing still another optical measuring apparatus embodying the present invention.

FIG. 15 shows still another example of measuring image colors, wherein as in the example of FIG. 13, a plurality of light sources are installed and instead of switching them over, there is provided a color filter 47 between the lens 43 and the photoelectric conversion element 44, so that a color filter switching means 48 is switched over, depending on the color of an image to be measured.

Like the example of FIG. 13, the density of an image of each color formed on the paper surface 37a can be measured by taking out the light reception output of the photoelectric conversion element 44 in synchronization with the switching of the color filter 47 and further colors of the full-color image can be evaluated by comprehensively calculating the measured results in the measurement computing unit.

Incidentally, the color filter 47 may be provided between the light source 41 and the paper surface 37a or between the paper surface 37a and the lens 43. Further, though FIG. 15 refers to the case where the paper surface 37a is irradiated with light from the light source 41 not via the lens 43, the arrangement shown in FIG. 15 is applicable likewise to even the case where the paper surface 37a is irradiated with light from the light source 41 via the lens 43.

When the opening 45 is provided as in the example of FIGS. 9 or 10, a color filter may be installed between the opening 45 and the photoelectric conversion element 44 and when the condenser lens 46 is provided as in the example of FIGS. 11 or 12, such a color filter may be installed between the condenser lens 46 and the photoelectric conversion element 44.

Figure 16:
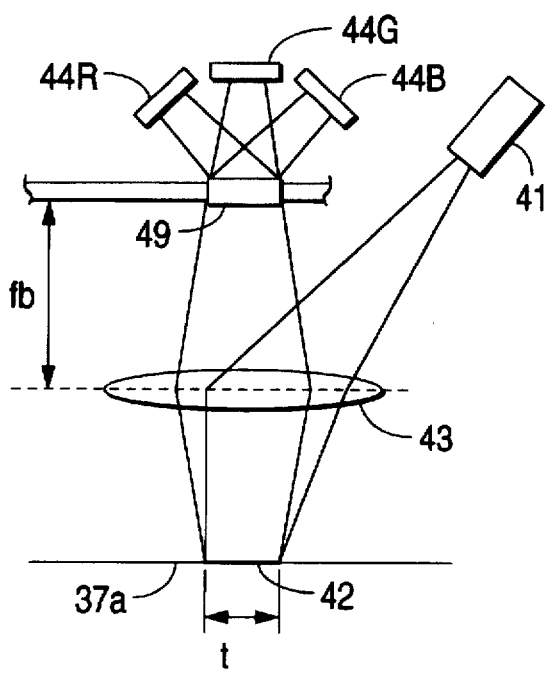
FIG. 16 is a diagram showing still another optical measuring apparatus embodying the present invention.

FIG. 16 shows a further example of measuring image colors, wherein when the opening 45 is provided as in the example of FIG. 10, a spectroscope 49 is installed at the position of the opening 45 so as to separate the light reflected from the paper surface 37a into red, green, blue color light and by causing different photoelectric conversion elements 44R, 44G, 44B to receive each kind of color, the density of an image of each color formed on the paper surface 37a is measured.

Although FIG. 16 refers to the case where the paper surface 37a is irradiated with light from the light source 41 via the lens 43, the arrangement shown in FIG. 16 is applicable likewise to even the case where the paper surface 37a is irradiated with light from the light source 41 not via the lens 43.

The spectroscope 49 may not be installed at the position of the opening 45 but at a position in the rearward of the opening 45. When the condenser lens 46 is installed as in the example of FIGS. 11 or 12, the same arrangement is applicable with the provision of the spectroscope at a position in the rearward of the condenser lens 46.

(Elimination of Influence of Disturbance Light)

In the aforementioned optical measuring apparatus, indoor illumination light other than light from the light source 41 may be incident on the photoelectric conversion element 44 as disturbance light. In this case, though it may be considered to cover the periphery of the apparatus with a casing in order to prevent the disturbance light from being incident on the photoelectric conversion element 44, the following arrangement is employed to ensure that the influence of such disturbance light is eliminated.

Figure 17:
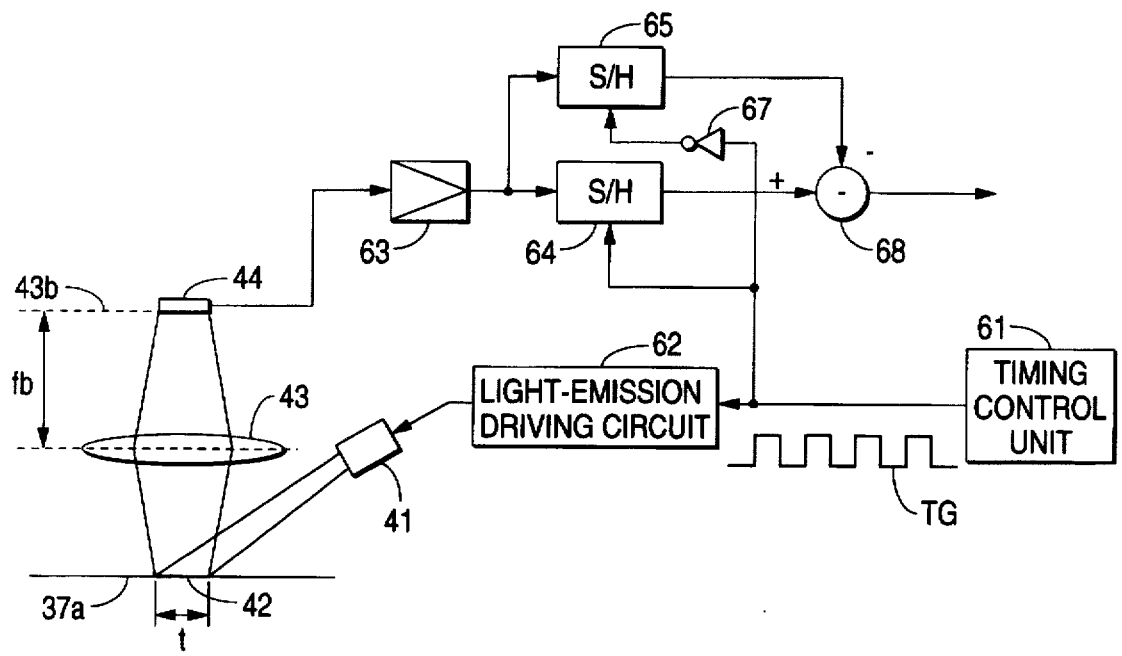
FIG. 17 is a diagram showing still another optical measuring apparatus embodying the present invention.

More specifically, FIG. 17 refers to a case where the influence of disturbance light is eliminated, wherein the light source 41 is blinked with a predetermined period and the light reception output of the photoelectric conversion element 44 is taken out in accordance with the blinking period, whereby the influence of disturbance light is removed.

In this example, a light emission timing signal TG alternately repeating high and low levels with a predetermined period is supplied from a timing control unit 61 to the light-emission driving circuit 62 of the light source 41, and the light source 41 is caused to emit light for the high-level period of the light emission timing signal TG so as to turn off the light source 41 during the low-level period.

Then, the light reception output of the photoelectric conversion element 44 is supplied via an amplifier 63 to two sample holding circuits 64, 65. To the sample holding circuit 64, the light emission timing signal TG is supplied as a sample holding signal, whereas to the sample holding circuit 65, a signal resulting from inverting the polarity of the light emission timing signal TG by a polarity inversion circuit 67 is supplied as a sample holding signal.

Therefore, the light reception output of the photoelectric conversion element 44 is sample-held in the sample holding circuit 64 for the high-level period of the light emission timing signal TG, and the light reception output is obtainable from the sample holding circuit 64 while the light source 41 is kept emitting light. The light reception output of the photoelectric conversion element 44 is sample-held in the sample holding circuit 65 for the low-level period of the light emission timing signal TG, and the light reception output is obtainable from the sample holding circuit 65 when the light source 41 is turned off.

The light reception output when the light source 41 is turned off is what is derived from only disturbance light, and the light reception component due to the disturbance light is contained in the output of the sample holding circuit 64.

Then the outputs of the sample holding circuits 64, 65 are supplied to a subtraction circuit 68, so that the difference therebetween is calculated. Consequently, a light reception output which is deprived of the light reception component produced by disturbance light but results from light only from the light source 41 is obtainable. Therefore, an accurate measured result unaffected by the disturbance light is obtainable from the output of the subtraction circuit 68.

In this case, by varying the light emission intensity of the light source 41 with a predetermined period, instead of blinking the light source 41, the light reception output of the photoelectric conversion element 44 may be taken out in harmony with the intensity thereof. Although the example of FIG. 17 has been applied to what is shown in FIG. 1, it is applicable to what is illustrated in FIG. 2 and those shown with reference to FIG. 9 and thereafter.

(Other Modes for Carrying Out the Invention or Embodiments of the Present Invention)

Although one lens 43 has been used in the aforementioned example, a plurality of lenses 43 may be used to form a lens system.

Moreover, a plurality of photoelectric conversion elements, for example, may be used to constitute the photoelectric conversion element 44 so as to take out the sum of light reception outputs therefrom. The use of a photoelectric conversion element having a large light reception area makes it difficult to obtain sufficient frequency response characteristics. However, not only sufficient frequency characteristics but also light reception outputs at a satisfactory level can be secured by the use of a plurality of photoelectric conversion elements each having a small light reception area in order to take out the sum of light reception areas.

Incidentally, the same effect may be achievable by adding up the light reception outputs at several positions by moving one photoelectric conversion element to a plurality of positions on the rear-side focal surface instead of providing a plurality of photoelectric conversion elements.

When the plurality of photoelectric conversion elements are thus installed on the rear-side focal surface or when one photoelectric conversion element is moved to the plurality of positions on the rear-side focal surface, light incident on the photoelectric conversion element at different positions is what is incident in different angular ranges out of the light reflected from the paper surface 37a. It is therefore possible to obtain the distribution of outputs of reflected light to the plurality of reflection angle ranges by reading the outputs of the photoelectric conversion elements at different positions to obtain such the distribution.

When light from the light source 41 may be reflected from a member for holding the lens 43 and incident on the photoelectric conversion element 44 as disturbance light, a diaphragm is preferably provided in front or in the rear of the lens 43 to check the disturbance.

FIG. 18 refers to a case where an image is measured by the optical measuring apparatus 40 at the position after fixation by means of the fixing device 36 in the image output unit 100 of the image forming apparatus. In this case, the image may be measured by the optical measuring apparatus 40 in the interval between the transfer by means of the transfer device 35 and the fixation by the fixing device 36.

Although FIGS. 18–19 shows examples of an image forming apparatus by electrophotography, the measurement of an image by the optical measuring apparatus 40 according to the present invention and the control of the image quality based on the light reception output are applicable to image forming apparatus of any other system such as an ink-jet and a thermal film system.

In an apparatus for conveying paper with an image formed thereon excluding process steps of forming images, the present invention is applicable to a case where the image formed on paper is measured during the conveyance of the paper and precise measurement becomes possible as in the case of applying it to such an image forming apparatus.

Moreover, the object of measurement is not necessarily limited to the paper mentioned in the examples above. Further, the object of measurement should not necessarily flat but may be what has an irregular surface and the characteristics of its reflection area can be measured precisely as long as the condition of Eq. (15) is satisfied. Therefore, the present invention is widely applicable to the measurement of not only images but also various characteristics of objects of measurement.

As described above, the surface properties of such an object of measurement can also be evaluated since the distribution of reflection angles of the light reflected from the object of measurement is obtainable when a plurality of photoelectric conversion elements are installed on the rear-side focal surface.

As set forth above, with the optical measuring method and the optical measuring apparatus according to the present invention, precise measurement can be made without being affected even when the movement of the object of measurement such as paper fluctuates in the direction of the optical axis of the lens. Particularly when the object of measurement is irradiated with light from the light source via the lens.

As the reflection area satisfying the specific limiting conditions is set up, the measured output fluctuation due to the fluctuation in the movement of the object of measurement in the direction of the optical axis of the lens like the vertically fluctuating movement of paper is reducible to zero, so that extremely precise measurement is achievable.

Since the optical measuring apparatus can be made small-sized and less costly, further, the quality of an image to be output is greatly improvable under feedback control through on-line measurement without increasing the size and cost of the apparatus.

The foregoing description of a preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An optical measuring method using a light source, a lens and a photoelectric conversion element which are disposed in such a manner that their relative positions are made mutually constant, said method comprising the steps of:

irradiating an object of measurement with light from said light source;

causing said photoelectric conversion element to receive the light reflected from said object of measurement via said lens;

measuring the characteristics concerning said object of measurement from the light reception output of said photoelectric conversion element;

setting a specific area large enough to receive part of the light passed through said lens and reflected from said object of measurement; and receiving only the light reflected from said object of measurement within a specific angular range equal to the specific area of said photoelectric conversion element via said lens so as to make the total quantity of light received by said photoelectric conversion element an output signal of said photoelectric conversion element.

2. An optical measuring method as claimed in claim 1, wherein said object of measurement is irradiated with light from said light source not via said lens.

3. An optical measuring method as claimed in claim 1, wherein said object of measurement is irradiated with light from said light source via said lens.

4. An optical measuring method as claimed in claim 1, wherein said light source is placed farther from said lens than said photoelectric-conversion-element-side focal surface of said lens.

5. An optical measuring method as claimed in claim 1, wherein said photoelectric conversion element which makes the area of said specific area a light reception area is installed on said photoelectric-conversion-element-side focal surface of said lens.

6. An optical measuring method as claimed in claim 1, wherein said specific area is an opening; and only light reflected from said object of measurement and passed through said opening is received by said photoelectric conversion element.

7. An optical measuring method as claimed in claim 1, wherein a condenser lens for making only light passed through said specific area incident on said photoelectric conversion element is installed in the position of said specific area.

8. An optical measuring method as claimed in claim 1, wherein the size of an area for reflecting light from said light source is set on said object of measurement in a range of conditions satisfying $$A \geq B+(C \times D)/f$$

where A=distance between the end of said lens and the optical axis of said lens, B=distance between the end of a reflection area of said object of measurement and said optical axis, C=distance between said lens and said reflection area, D=distance between the end of said specific area and said optical axis, and f=focal length of said lens.

9. An optical measuring apparatus comprising:

a light source for irradiating an object of measurement with light;

a lens having an optical axis in a direction different from an incident direction of light from said light source, part of the light reflected from said object of measurement being incident on said lens; and a photoelectric conversion element so positioned that out of the light reflected from said object of measurement and passed through said lens, said element receives only the reflected light within a specific angular range determined by the reflected light reception area in the position of the focal surface of said lens opposite to said object of measurement, the photoelectric conversion element makes the total quantity of light received an output signal of said photoelectric conversion element;

wherein said light source, said lens and said photoelectric conversion element are disposed in such a manner that their relative positions are made mutually constant;

wherein the relative position of said object of measurement with respect to said light source, said lens and said photoelectric conversion element varies in the direction of the optical axis of at least said lens; and wherein characteristics concerning said objects of measurement are measured from the output of said photoelectric conversion element.

10. An optical measuring apparatus as claimed in claim 9, wherein said object of measurement is irradiated with light from said light source not via said lens.

11. An optical measuring apparatus as claimed in claim 9, wherein said object of measurement is irradiated with light from said light source via said lens.

12. An optical measuring apparatus as claimed in claim 9, wherein said light source is placed farther from said lens than said photoelectric-conversion-element-side focal surface of said lens.

13. An optical measuring apparatus as claimed in claim 9, wherein the size of an area for reflecting light from said light source is set on said object of measurement in a range of conditions satisfying $$A \geq B+(C \times D)/f$$

where A=distance between the end of said lens and the optical axis of said lens, B=distance between the end of a reflection area of said object of measurement and said optical axis, C=distance between said lens and said reflection area, D=distance between the end of the light reception area of said optical axis, and f=focal length of said lens.

14. An optical measuring apparatus as claimed in claim 9, including means for controlling said light source so as to emit light by blinking or varying light intensity, and means for obtaining the light reception output of said photoelectric conversion element in synchronization with the blinking of said light source or variation in light intensity.

15. An optical measuring apparatus as claimed in claim 9, wherein said photoelectric conversion element, said second lens or said opening is installed in different positions, said second lens or said opening is moved to a plurality of positions within said photoelectric-conversion-element-side focal surface of said lens or said first lens, so that characteristics concerning said object of measurement are measured from the total of the light reception outputs in the plurality of positions.

16. An optical measuring apparatus as claimed in claim 9, wherein an optical filter is provided within a light passage from said light source and said photoelectric conversion element, so that colors of said object of measurement are measured from the light reception output of said photoelectric conversion element.

17. An optical measuring apparatus as claimed in claim 9, wherein a plurality of light sources different in wavelength of light to be emitted are installed; and means for obtaining the light reception outputs of said photoelectric conversion element separately on a light source basis with respect to the light emitted from the plurality of light sources and reflected from said object of measurement so that colors of said object of measurement are measured.

18. An optical measuring system wherein a plurality of optical measuring apparatus as claimed in claim 9 are disposed for one object of measurement; the wavelengths of light emitted from said light sources of the plurality of optical measuring apparatus are made mutually different, so that colors of said object of measurement are measured from the light reception outputs of said photoelectric conversion elements of the plurality of optical measuring apparatus.

19. An image forming apparatus comprising: an optical measuring apparatus as claimed in claim 9 installed in a passage in which an image forming medium as said object of measurement with the image formed by image forming means is conveyed; and control means for controlling the quality of an image to be formed on said image forming medium on the basis of the results measured by said optical measuring apparatus or said optical measuring system.

20. An optical measuring apparatus comprising:

a light source for irradiating an object of measurement with light;

a first lens having an optical axis in a direction different from an incident direction of light from said light source, part of the light reflected from said object of measurement being incident on said first lens;

a second lens or an opening so positioned that out of the light reflected from said object of measurement and passed through said first lens, said second lens transmits only the light reflected within a specific angular range determined by the reflected light area in the position of the focal surface of said lens opposite to said object of measurement; and an photoelectric conversion element for receiving the light transmitted through said second lens or said opening and making the total quantity of light received an output signal of said photoelectric conversion element;

wherein said light source, said first lens, said second lens or said opening and said photoelectric conversion element are disposed in such a manner that their relative positions are made mutually constant;

wherein the relative position of said object of measurement with respect to said light source, said first lens, said second lens or said opening and said photoelectric conversion element varies in the direction of the optical axis of at least said first lens; and wherein characteristics concerning said object of measurement are measured from the output of said photoelectric conversion element.

21. An optical measuring apparatus as claimed in claim 20, wherein said object of measurement is irradiated with light from said light source not via said first lens.

22. An optical measuring apparatus as claimed in claim 20, wherein said object of measurement is irradiated with light from said light source via said first lens.

23. An optical measuring apparatus as claimed in claim 22, wherein said light source is placed farther from said first lens than said photoelectric-conversion-element-side focal surface of said first lens.

24. An optical measuring apparatus as claimed in claim 20, wherein the size of an area for reflecting light from said light source is set on said object of measurement in a range of conditions satisfying $$A \geq B + (C \times D)/f$$

where A=distance between the end of said first lens and the optical axis of said first lens, B=distance between the end of a reflection area on said object of measurement and said optical axis, C=distance between said first lens and said reflection area, D=distance between the end of said second lens or said opening and said optical axis, and f=focal length of said first lens.

25. An optical measuring apparatus as claimed in claim 20, wherein light arriving at said second lens or said opening is detected by a spectroscope, so that colors of said object of measurement are measured.

* * * * *